United States Patent
Ramos Murguialday et al.

(10) Patent No.: US 11,259,942 B2
(45) Date of Patent: Mar. 1, 2022

(54) SYSTEM FOR MOTOR REHABILITATION OF A PARETIC LIMB IN STROKE PATIENTS

(71) Applicants: FUNDACION TECNALIA RESEARCH & INNOVATION, San Sebastián (ES); THE REGENTS OF THE UNIVERSITY OF CALIFORNIA, Oakland, CA (US); EBERHARD KARLS UNIVERSITAET TUEBINGEN, Tuebingen (DE)

(72) Inventors: Ander Ramos Murguialday, Tuebingen (DE); Niels Birbaumer, Moessingen (DE); Jose Miguel Carmena Ramon, Alameda, CA (US)

(73) Assignees: FUNDACION TECNALIA RESEARCH & INNOVATION, San Sebastian (ES); THE REGENTS OF THE UNIVERSITY OF CALIFORNIA, Oakland, CA (US); EBERHARD KARLS UNIVERSITAET TUEBINGEN, Tuebingen (DE)

( * ) Notice: Subject to any disclaimer, the term of this patent is extended or adjusted under 35 U.S.C. 154(b) by 281 days.

(21) Appl. No.: 15/526,680

(22) PCT Filed: Nov. 14, 2014

(86) PCT No.: PCT/US2014/065703
§ 371 (c)(1),
(2) Date: May 12, 2017

(87) PCT Pub. No.: WO2016/076886
PCT Pub. Date: May 19, 2016

(65) Prior Publication Data
US 2017/0325705 A1 Nov. 16, 2017

(51) Int. Cl.
*A61B 5/316* (2021.01)
*A61F 2/72* (2006.01)
(Continued)

(52) U.S. Cl.
CPC .............. *A61F 2/72* (2013.01); *A61B 5/1122* (2013.01); *A61B 5/1124* (2013.01);
(Continued)

(58) Field of Classification Search
CPC ............ A61B 5/04888; A61B 5/04012; A61B 5/1122; A61B 5/1124; A61B 5/1126;
(Continued)

(56) References Cited

U.S. PATENT DOCUMENTS 9,579,060 B1 * 2/2017 Lisy ........................ A61B 5/302
2008/0288020 A1 * 11/2008 Einav ................. A61N 1/36003
607/48

(Continued)

OTHER PUBLICATIONS

International Search Report and Written Opinion of the International Searching Authority, Search Report, Application No. PCT/US2014/065703 issued by the European Patent Office, Rijswijk, Netherlands, dated Jul. 23, 2015.

(Continued)

*Primary Examiner* — Robert P Bullington
(74) *Attorney, Agent, or Firm* — Peter B. Scull; EIP US LLP

(57) ABSTRACT

A system or method for motor rehabilitation of a paretic limb including:
  a first plurality of sensors for registering brain neurosignals;
  a body-actuator;
  a hybrid brain machine interface for decoding brain neurosignals into movements of the body-actuator;
  a second plurality of EMG sensors couplable to the paretic limb for registering its EMG activity;
(Continued)

a device for providing the patient with instructions relative to a series of exercises and/or tasks to be carried out with the paretic limb;

wherein upon carrying out a series of training sessions, each session comprising at least a set of such instructions, the hybrid brain machine interface is configured to switch between controlling the movements of the body-actuator based on the decoded brain neurosignals and a hybrid control of the movements of the body-actuator, when a significant level of decodable EMG activity has been registered, the hybrid control being an EMG-gated brain control.

19 Claims, 3 Drawing Sheets

(51) Int. Cl.
    *A61B 5/11*       (2006.01)
    *A61B 5/00*       (2006.01)
    *G09B 5/02*       (2006.01)
    *G09B 19/00*     (2006.01)

(52) U.S. Cl.
    CPC ............ *A61B 5/1126* (2013.01); *A61B 5/316* (2021.01); *A61B 5/486* (2013.01); *A61B 5/4851* (2013.01); *G09B 5/02* (2013.01); *G09B 19/003* (2013.01); *A61B 5/40* (2013.01); *A61B 5/6868* (2013.01); *A61B 2505/09* (2013.01)

(58) Field of Classification Search
    CPC ......... A61B 5/486; A61B 5/40; A61B 5/6868; A61B 2505/09; A61B 5/316; A61B 5/4851; G09B 5/02; G09B 19/003; G09B 12/00; A61F 2/72

USPC .................. 434/272, 247; 600/383, 27, 544; 607/54; 601/5

See application file for complete search history.

(56) References Cited

U.S. PATENT DOCUMENTS

| | | | |
|---|---|---|---|
| 2009/0221928 A1* | 9/2009 | Einav ................... | A61B 5/0484 600/544 |
| 2014/0031711 A1* | 1/2014 | Low ..................... | A61B 5/4076 600/544 |
| 2014/0031952 A1* | 1/2014 | Harshbarger ............. | A61F 2/54 623/25 |
| 2014/0142474 A1* | 5/2014 | McBean ............... | A61F 5/0127 601/33 |
| 2014/0200432 A1 | 7/2014 | Banerji et al. | |
| 2014/0212243 A1* | 7/2014 | Yagi ....................... | A61H 1/024 414/2 |
| 2014/0277582 A1* | 9/2014 | Leuthardt ................. | A61F 2/72 623/25 |
| 2015/0012111 A1* | 1/2015 | Contreras-Vidal .. | A61B 5/4851 623/25 |
| 2015/0289995 A1* | 10/2015 | Wilkinson ................ | A61F 2/70 623/27 |
| 2016/0128890 A1* | 5/2016 | LaChappelle ............. | A61F 2/70 623/30 |
| 2017/0143229 A1* | 5/2017 | Weffers-Albu ...... | A61B 5/4519 |

OTHER PUBLICATIONS

Thilina Dulantha Lalitharatne et al: "Abstract", Paladyn, Journal of Behavioral Robotics, Dec. 10, 2013, pp. 147-154, vol. 4, No. 2, XP055201600, ISSN: 2081-4836, DOI: 10.2478/pjbr-2013-0009, De Gruyter Open Ltd. formerly Versita, Warsaw, Poland.

* cited by examiner

SYSTEM FOR MOTOR REHABILITATION OF A PARETIC LIMB IN STROKE PATIENTS

TECHNICAL FIELD

The present developments relate to the field of motor training and/or rehabilitation, especially for chronic stroke patients.

BACKGROUND

The cerebro-vascular accident caused by stroke, brain injury, or cerebral paralysis is one of the main causes of long-term motor disability worldwide and in more than 85% of these cases functional deficits in motor control occur. Incidence of first stroke in Europe is about 1.1 million and prevalence about 6 million. Of all stroke survivors showing no active upper limb motion at hospital admission 14% showed complete recovery, 30% showed partial recovery and 56% show little or no recovery, and the grand majority retained sensory function.

Standard and commonly used functional and activity level assessments in stroke like Fugl-Meyer and other known tests, despite their proven reliability, validity, and responsiveness, are highly subjective and depend directly on the therapist and sometimes on the patient (self-rating).

Movement is produced by a pattern of muscle activity normally distributed among different muscles. Dysfunction in a muscle involved in a motor movement results in inaccuracy. Overactivity of antagonistic muscles could even lead to total paralysis of the affected limb.

Spasticity, or continuous overcontraction of the muscles, is a handicap a stroke patient needs to overcome in order to produce the desired movement and could be one of the main causes of continued impairment besides the complete damage of the corticospinal tract. In the paralyzed arm extensor muscles are mostly paralyzed after stroke and flexors are more affected from spasticity. Thus patients are unable to open their hand and reach forwards to grasp.

The cessation of activity in extensor muscles after stroke is commonly accepted for paralyzed patients. If there are residual EMG signals present, these are mostly extremely small, partially involuntary and resulting in inaccurate motions. Such dysfunction leads to a reduction in muscle use (learned non-use) and muscle atrophy.

In order to overcome the absence of appropriate control of paretic muscles in stroke patients, new rehabilitation therapies based on neural signals and robotic devices have been proposed.

Over the past years, an increasing number of brain machine interface (BMI) systems have been developed. These systems record, decode, and ultimately translate some measurable neurophysiological signal into an effector action or behaviour. Using microelectrode implants in various cortical areas, monkeys and humans were trained to control robotic arms for reaching and grasping during feeding.

Interestingly, it has been proposed that the combination of robotics and brain control of upper limb assistive technology could contribute to improve neurorehabilitation.

One limitation of the use of control signals originated in the brain so far has been that the decoding performance using non-invasive brain signals like electroencephalogram (EEG), magnetoencephalogram (MEG), or functional near infrared spestroscopy (fNIRS) is limited.

The fact is that currently there is no accepted and efficient rehabilitation strategy available that aims at reducing focal impairments in patients with chronic stroke and no residual hand movements because residual movements are needed to produce a control signal (force or/and movement).

SUMMARY

The present developments refer to a system for motor rehabilitation of a paretic limb of a patient which links assisted movement of the paretic limb by a body-actuator with the cortical activity generated during this movement in order to promote functional neural pathways through a process based on neuroplasticity.

Through use of a system of the present disclosure, and after a number of training sessions, neural circuits inducing motor recovery in a certain group of stroke patients are generated. That is, new neural connections are established between the brain and the paralyzed muscles of the patient within the central and peripheral nerve system circumventing the lesions and thereby allowing functional motor rehabilitation.

The system for motor rehabilitation of a paretic limb of a patient may include:

a first plurality of sensors couplable to pre-established positions of a head of the patient for registering brain neurosignals of the patient;

a body-actuator couplable to, at least, a paretic limb of the patient;

a hybrid brain machine interface for decoding the brain neurosignals into movements of the body-actuator;

a second plurality of EMG sensors couplable to the paretic limb of the patient, for registering EMG activity of the paretic limb of the patient;

one or more devices for providing the patient with instructions relative to a series of exercises and/or tasks to be carried out with the paretic limb;

wherein upon carrying out a series of training sessions, each session comprising at least a set of such instructions, the hybrid brain machine interface is configured to establish a transition between controlling the movements of the body-actuator based on the decoded brain neurosignals and whenever a significant level of decodable EMG activity has been registered, controlling the movements of the body-actuator, by a hybrid control which is an EMG-gated brain control.

In a system hereof, the body actuator can be a device based on FES—functional electrical stimulation—or a robotic exoskeleton.

And the first plurality of sensors for registering the brain neurosignals are any or a combination of the following: an array of intracortical microelectrodes, a plurality of wireless ECoG (Electrocorticography) micro- or nano-electrodes, a plurality of EEG (Electroencephalography) sensors or any brain imaging system based on fMRI (functional magnetic resonance imaging) or fNIRS (functional near infrared).

The first plurality of sensors is preferably couplable in the motor cortex or in perilesional cortical areas.

The one or more devices for providing the patient with instructions relative to a series of exercises and/or tasks to be carried out with the paretic limb may preferably include any device (or devices) including a screen or display and any sort of loudspeaker or headphone which present visual and auditory cues to the patient with instructions and/or imperative orders to execute a task. The device may present objects to the patient in a random but controlled manner, in such a way that the system knows at all times the task presented to the patient, and therefore, what the final limb posture should be, and is able to estimate the trajectory, which can be used to tune the brain machine interface at the beginning of each session.

Having registered a significant level of decodable EMG activity of the paretic limb is indicative of a working new neural circuit being generated or of an existing malfunctioning corticomuscular connection being reinforced by having excited the central and peripheral nervous system of the patient.

It is preferably considered that a significant level of decodable EMG activity has been registered when either a pre-established level of decodable EMG activity of the paretic limb or a pre-established level of decodable EMG accuracy between rest and activity of the paretic limb has been registered.

The significant level of decodable EMG activity is preferably determined by comparing the decoded EMG activity of the paretic limb with a first reference EMG activity. This first reference EMG activity can be the EMG activity during rest of the paretic limb or the EMG activity of a healthy limb.

In a preferred implementation the EMG-gated brain control includes modulating the decoded brain neurosignals with a variable weighting factor, the weighting factor being a function of the decoded EMG activity of the paretic limb.

Preferably, the weighting factor is a function of a difference between the decoded EMG activity of the paretic limb and a second reference activity model.

The second reference activity model is preferably the decoded EMG activity of a healthy limb of the patient, recorded prior to the training session or as retrieved from a database.

The second reference activity model can also be the trajectory as decoded from the brain activity only, and the weighting factor being a difference between this trajectory and the trajectory calculated from the decoded EMG activity during the same exact movement.

The efficacy of a system hereof may be based on a training protocol based on neural/hebbian plasticity and instrumental learning, and a brain translation algorithm included in the hybrid brain machine interface (hybrid BMI, which combines brain neurosignals and EMG signals), which establishes a transition between brain control and an EMG-gated brain control of the body-actuator.

The relevance of the EMG activity is gradually increased thereby shifting from brain control to muscle control.

A system for motor rehabilitation of an impaired or paretic limb hereof may be based on a totally unique link between the patient's neural signals and the movements of the limb muscles affected by the paresis, and the modulation and reorganization of neural processes using a brain-body linked actuator which enables instrumental learning by assisted movement of the paretic arm. This modulation and reorganization is achieved by the hybrid brain machine interface that induces and controls the reorganization of brain processes adaptively by natural (visual, haptic and proprioceptive) stimulation of brain regions related to the impairment.

A second aspect hereof refers to a method for motor rehabilitation of a paretic limb of a stroke patient, which may include:
  placing a first plurality of sensors at pre-established positions of a head of the patient for registering brain neurosignals of the patient;
  coupling a body-actuator to, at least, a paretic limb of the patient;
  connecting a hybrid brain machine interface to the first plurality of sensors and to the body-actuator and decoding neurosignals into movements of the body-actuator;
  placing a second plurality of EMG sensors for registering EMG activity of the paretic limb of the patient and connecting this second plurality of EMG sensors to the hybrid brain machine interface;
  providing the patient with instructions relative to a series of exercises and/or tasks to be carried out with the paretic limb;
  carrying out a series of training sessions, each session comprising at least a set of such instructions, and
  when a significant level of decodable EMG activity has been registered the hybrid brain machine interface switches between controlling the movements of the body-actuator based on the decoded brain neurosignals and a hybrid control of the movements of the body-actuator, the hybrid control being an EMG-gated brain control.

Each training session is divided in several phases preferably defining completion of the exercise and/or task going from simple to more complex movements, or following a proximal-to-distal approach.

Preferably, the time elapsed between the register of the neurosignals and their decoding by the BMI into movements of the body-actuator is below 1 s; more preferably it is in the order of 20-100 ms.

A method for motor rehabilitation hereof proposes a multi-phase rehabilitation process depending of the cortical innervation levels of the affected muscles:
  1) brain control is used when no muscle control is present. If muscle activity is present a hybrid control based on muscle and brain activity is used to link brain activity due to intention to produce a movement and that same movement promoting correct EMG activity generation. This enhances and improves existing residual corticomuscular connections;
  2) after some rehabilitation sessions with a system hereof new neural circuits (via instrumental learning) are induced which circumvent the paresis and allow brain signals from cortical areas to reach the paralyzed muscles, inducing detectable EMG activity;
  3) at a final phase of rehabilitation, brain signals from cortical areas reach the paralyzed muscles more efficiently, inducing controllable EMG activity and using the new neural circuit generated which closes the loop between the brain and the limb movement and generates functional motor rehabilitation.

After this final phase of rehabilitation when a plateau or a maximum level of improvement in the patient has been reached (once those new neural circuits have been created which circumvent the paresis and allow the brain signals to reach the paralyzed muscles), all the components of a system hereof can be definitely removed from the patient; or if intracortical or wireless microelectrodes have been implanted in the patient's head, the electrodes are not removed (since their removal could produce damage in the neural tissue surrounding them) but the rest of components are, and the patient is nevertheless able to move the paretic limb on their own as if he/she were using a system of the present disclosure.

The different aspects and embodiments hereof defined herein can be combined with one another, as long as they are compatible with each other.

Additional advantages and features will become apparent from the detailed description that follows and will be particularly pointed out in the appended claims.

BRIEF DESCRIPTION OF THE DRAWINGS

To complete the description and in order to provide for a better understanding of the present subject matter, a set of drawings is provided. Said drawings form an integral part of the description and illustrate an implementation hereof, which should not be interpreted as restricting the scope of the invention or the claimed subject matter, but just as an example of how the invention and/or subject matter hereof can be carried out. The drawings comprise the following figures:

DETAILED DESCRIPTION

The following description is not to be taken in a limiting sense but is given solely for the purpose of describing the broad principles of the present disclosure. Next implementations hereof will be described by way of example, with reference to the above-mentioned drawings showing elements and results according hereto.

Figure 1:
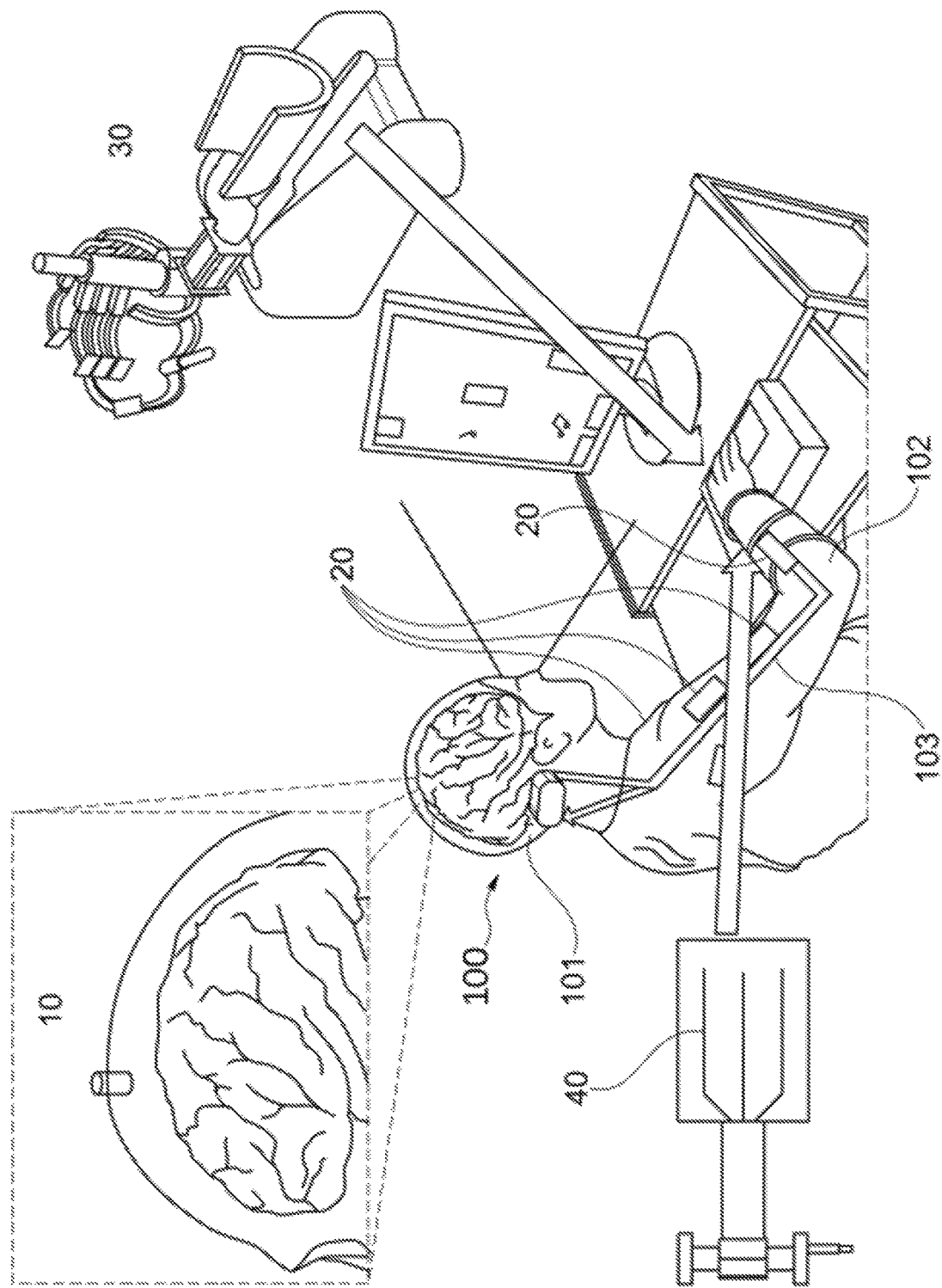
FIG. 1 shows a preferred implementation of a system for limb motor rehabilitation according to the present disclosure.

As shown in FIG. 1, a system hereof may include a hybrid brain machine interface BMI 200—not represented in FIG. 1—connected to an array of intracortical microelectrodes 10 installed in the head 101 of a patient 100. The hybrid brain machine interface BMI is also connected to a body actuator which in the example shown may include a robotic exoskeleton 30 (an ArmAssist exoskeleton by Tecnalia) and a device based on FES 40 positioned at the fore-arm 102 and upper-arm 103 of the patient 100.

It is also possible to use as body actuator any device, which may be implanted in the body, which is able to move a part of the body by controlling spinal cord stimulation or deep brain stimulation.

The hybrid BMI also is connected to a plurality of EMG sensors 20, which in the example shown in FIG. 1 are surface electrodes, coupled to the patient's upper- and fore-arms, thereby receiving EMG signals from the paretic arm.

As indicated, in the implementation shown in FIG. 1 the sensors for registering brain neurosignals used are intracortical microelectrodes 10. But it is also possible to register the brain neurosignals by blood oxygenation level-dependent (BOLD) signals, using both functional near-infrared spectroscopy (fNIRS) and functional magnetic resonance imaging (fMR), and magnetoencephalography (MEG), electroencephalo-graphy (EEG), deep brain electrodes, ultrasound, and/or any neuroimaging technique or the combination of any of them.

A system hereof may be used in a series of training sessions, each session comprising a set of instructions relative to a series of exercises and/or tasks to be carried out with the paretic limb.

Figure 2:
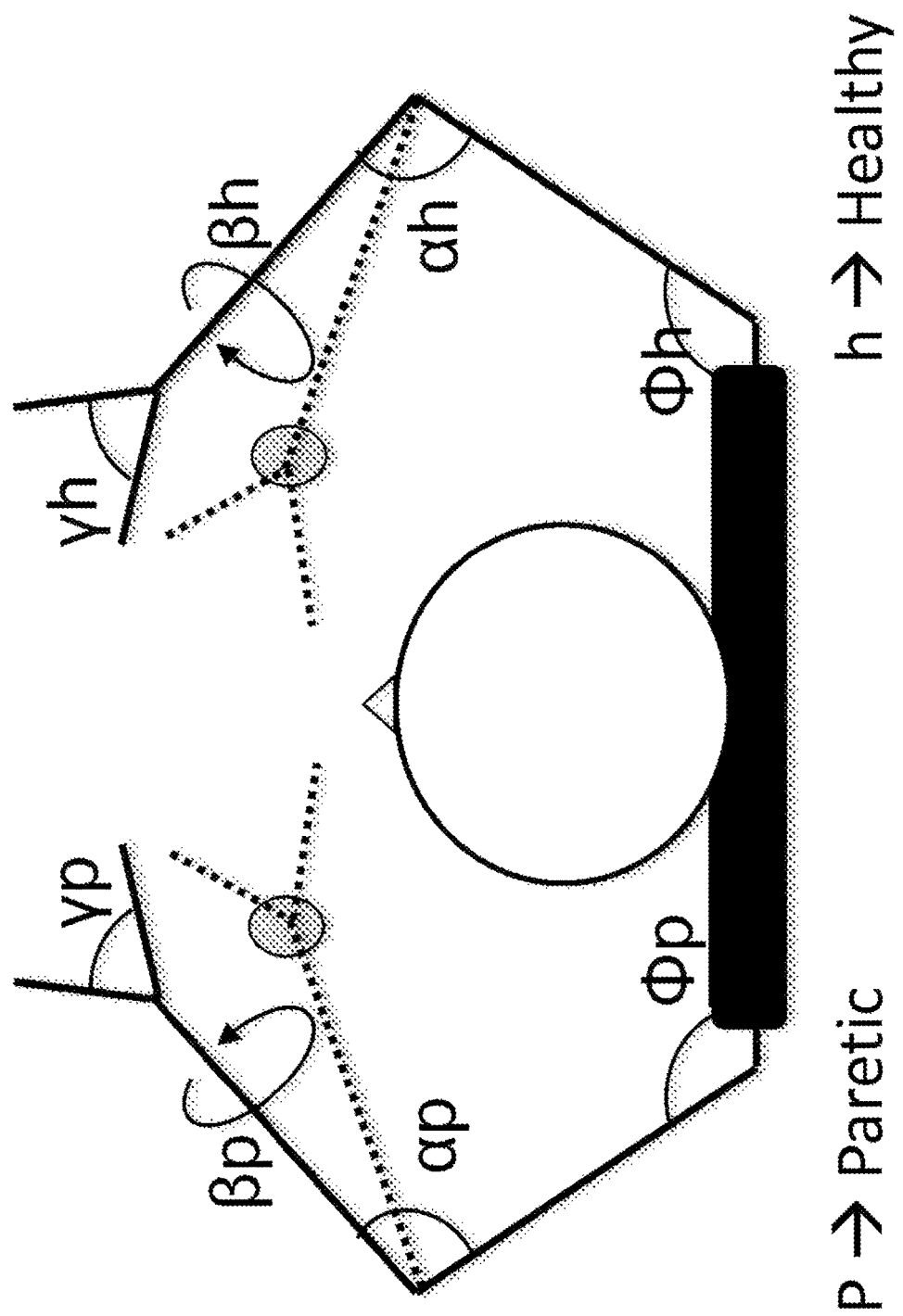
FIG. 2 schematically shows the equivalent movements made by both the healthy and the paretic arms from an equivalent starting position (shown by a continuous line) to an equivalent target position (shown by a dotted line).

As shown in FIG. 2, the brain neurosignals as detected by the intracortical microelectrodes 10 when the patient tries to move to accomplish one of the specific tasks in the training session (for example, moving from a first position to a target position, and then grasping) are input to the movement decoder (brain signal decoder) of the BMI which decodes such neurosignals into a set of kinematic features or parameters which define the desired body actuator control.

For instance, the hybrid BMI outputs angular velocities/accelerations of each of the body actuator joints: shoulder extension $\phi$, elbow extension $\alpha$, pronation/supination $\beta$ and hand open/close $\gamma$.

Any type of decoding, such as CLDA (closed-loop decoder adaptation), linear regression or any kind of machine learning technique can be used to translate the brain activity of the patient as registered by the intracortical microelectrodes 10 into such kinematic features or parameters which define the movement of the patient's paralyzed limb.

It is important that the time elapsed between the brain neurosignals are processed and the corresponding set of kinematic features or parameters is sent to the body actuator is in the order of 20-100 ms, and in any case below 1 s, so that the patient interprets the movements imposed by the robotic exoskeleton 30 as if they were his/her own.

At the same time the patient tries to induce the movements indicated in the task, thereby evoking some EMG limb neurosignals—if present at all—. In the case of severe patients, these EMG neurosignals of the paretic limb are almost negligible and during the first sessions the hybrid BMI of the system just uses the decoded patient's brain neurosignals to control the robotic exoskeleton 30 and/or the FES 40. In the case of less severe patients with minimally active corticomuscular connections, there is already decodable residual EMG activity in their affected limbs. In these patients, the FES 40 helps to strengthen the muscle and improves EMG detection.

In any case, after some rehabilitation sessions with a system hereof, either a predefined level of decodable EMG activity of the paretic arm or a pre-established level of decodable EMG accuracy between rest and activity of the paretic limb is reached. The EMG activity is decoded using, for example, a time domain feature like waveform length.

This predefined level is the minimum level of EMG activity of the paretic limb so that not only noise is input in the BMI's movement decoder when such EMG signals are added.

In order to know whether this predefined level of EMG activity has been reached, the decoded EMG activity is compared to a first reference EMG activity.

This first reference EMG activity can be the decoded EMG activity of the paretic arm during rest, as previously registered. Or it can also be a decoded EMG activity of the healthy arm which gives information regarding the EMG activation level at each electrode recorded on top of the different muscles, and the relevance of this activity for the execution of each movement.

Thus, the decoded EMG activity is compared to this first reference EMG activity of the paretic during rest or of the healthy arm, and analysed whether this EMG activity is taking place under control of the patient or whether it is the result of reflexes, spasticity spasms, etc. This analysis can be carried out by statistical means such as T—student tests or with classifiers such as neural networks (NNs) or with support vector machines (SVMs).

In fact, the achievement of this level of EMG activity or EMG decoding accuracy of the paretic limb is indicative of a new neural circuit being generated—in the case of severe patients—or the reinforcement of existing minimally active corticomuscular connections—in the case of less severe patients—, by having sufficiently and correctly excited the central nervous system of the patient.

Thus, when the predefined level of decodable EMG activity in the paretic limb or the pre-established level of decodable EMG accuracy between rest and activity of the paretic limb is reached (for instance, 65%), the hybrid BMI switches to a hybrid control and starts using both the decoded brain neurosignals and also the decoded EMG limb neurosignals to control the robotic exoskeleton 30 and/or the FES 40. This analysis of the EMG activity registered on the paretic limb during each training session is carried out, normally offline, to prove there is significant EMG activity during the movement, that is, that there is consistent and significant muscle contraction during the movement and that this is different than resting EMG activity. In this case 65% has been chosen since it is considered to be the minimum level of acceptable control of the body actuator.

That is, the hybrid BMI starts using an EMG-gated brain control of the movements of the robotic exoskeleton 30 and/or the FES 40. This EMG-gated brain control includes modulating the set of kinematic features or parameters (as output of the brain neurosignals decoder) by a variable weighting factor, the weighting factor being a function of the decoded EMG activity of the paretic limb.

This decoded EMG activity of the paretic limb is quantified, for example, using cocontraction levels, EMG data transformed into frequency or time domain features or antagonistic muscles ratio, etc. And it is compared (for example, using linear regressions) to a second reference activity model. This second reference activity model can be the EMG activity of the paretic limb previously registered offline. The second reference activity model can also be, for example, the EMG activity during those exact equivalent movements but performed with the healthy arm.

Healthy EMG activity, or EMG activity from the healthy arm, can be first recorded actively performing the rehabilitation movements using the body actuator. This healthy EMG activity can be used to calculate, for example, an antagonistic muscle pair ratio. Or it can also be used to decode movement (discrete decoding) or movements' trajectories (continuous decoding) using any decoding algorithm, such as Artificial Neural Networks, Support Vector Machines, Linear Regressions . . . ).

The difference in EMG activity (measured by antagonistic muscle pair ratio or trajectory decoding) of the paretic arm at each electrode during a BMI driven movement compared to the one obtained in the equivalent electrode on the healthy limb during the equivalent movement (i.e. equivalent to the trajectory decoded from brain activity only: taken as ground truth of movement intention) is used to calculate the weighting factor. The weighting factor modulates the corresponding output (i.e. kinematic parameter to control the body actuator e.g. $\phi$, $\alpha$, $\beta$ and $\gamma$) in the BMI's movement decoder, previously calculated using brain activity only.

The computed weighting factor is normalized (for example, between 0.5 and 1.5; 0.5 when there is no correspondence between the healthy and the paretic arms and 1.5 when there is perfect match between them) for each specific kinematic parameter, and then it multiplies the corresponding control signal parameter which has been obtained using only the brain activity. For example, if significant EMG activity is detected at the antagonistic muscle pair (for example, triceps and biceps), the correspondent angular velocity of the movement produced by those muscles— elbow extension $\alpha$ in the case of the triceps/biceps antagonistic pair)—is weighted.

Another option could be to sum both the resulting brain only and muscle only output kinematic control vectors (e.g. velocities of each motor in the body actuator) and use this sum as final weighted decoder output vector.

This way each control signal of the body-actuator previously computed only with brain signals is modulated with the muscle activity of the paretic limb as registered by the EMG sensors, thereby preventing that the brain control is so simple that the patients do not need to use the muscles to activate the body-actuator and can control it by merely thinking of that movement, or learning how to regulate their neuron firing without involving corticomuscular connection in the process: the patient needs to do some muscle contraction to operate the body-actuator.

In any case, the control of the brain activity during the intention to produce a specific movement is the ground truth of the patient's intention, that is, the brain neurosignals prevail over the decoded EMG activity; however, minimal, residual and erratic EMG activity conditions the functioning of the hybrid BMI decoder.

By modifying the variable weighting factor the level of EMG activity of the paretic limb is gradually increased to reflect the increased relevance of the EMG input related to muscle activity in the hybrid BMI. However, this shift might not be linear since the final goal is to have a supervised control of the body actuators, which needs muscle activity as a requirement for their activation and cortical activity to supervise that the muscle contraction is not due to compensatory movements but to correct synergistic muscle activity.

As previously indicated, the decoded brain activity is used always as "ground truth" of the motor intention of the patient and as control for proper muscle activation during the EMG-weighted brain decoding control: for example, proper activation of patterns of muscle activity (muscle synergies) and not activation of a single muscle which could lead to biased decoding of erratic movements. If feedback of this erratic movement is provided as a proper movement the system fails to induce the proper muscle activity, and therefore brain supervision is necessary.

In fact, the contingent artificial connection between brain signals and body actuators stimulates the afferent pathways involved in a visuomotor task bridging the gap between the brain signals due to an intention to move and that same movement. The feedback perceived by the patient from his brain activity modulation while trying to move produces the generation of new neural circuits either via axonal sprouting or rewiring existing neural connections due to hebbian and instrumental learning driven plasticity. These new neural circuits connect supraspinal cortical areas responsible for volitional movement generation with the muscles responsible for that same movement, generating motor recovery.

Figure 3:
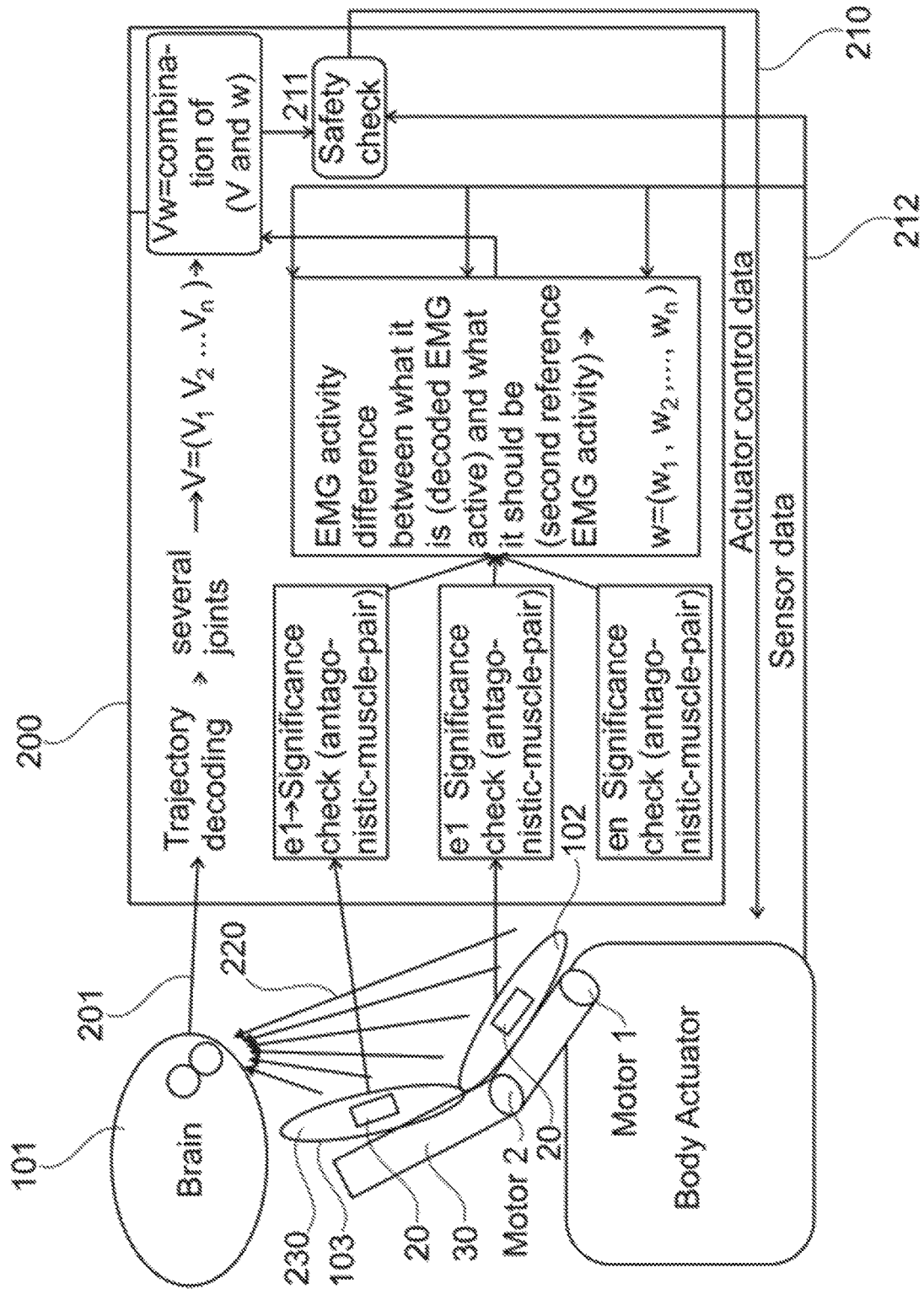
FIG. 3 schematically shows how the hybrid BMI operates.

FIG. 3 schematically shows an example of how the recorded brain and muscle activities are merged in the hybrid BMI 200.

In this example, the brain neurosignals from the intracortical microelectrodes 10 when the patient tries to do the task or exercise are inputted (arrow 201) in the hybrid BMI and decoded as a velocity vector "V" of every joint of the robotic exoskeleton 30, which has as many terms as degrees of freedom (motors) of the robotic exoskeleton 30, $V=(V_1, V_2, \ldots, V_n)$.

If there is no significant EMG activity as registered in the previous training session, the output of the hybrid BMI is the velocity vector V as indicated above.

However, if any of the electrodes 20 (e1 in the upper-arm, e2 in the fore-arm) presents significant EMG activity in the previous session, this EMG activity of the paretic limb is compared to the EMG activity obtained from the healthy arm when performing the same movement (mirrored) and is used as weighting factor "w" for the velocity vector "V".

This can be done by comparing the EMG activity (activity ratio between antagonistic muscle pairs, or each electrode activity) during that movement in the healthy and the paretic arms and generating a weighting factor w that takes into account not only a normalized difference in EMG activity between the paretic and healthy arms, but also the influence of that muscle (i.e. electrode) activity in the overall movement performed by the body actuator (i.e. influence in each motor of the body actuator).

This weighting factor vector w can multiply the velocity vector V obtained by the movement decoder of the BMI using only brain activity to obtain a new weighted velocity vector Vw, Vw=V*w.

Another option could be to decode the trajectory with whatever EMG is available (i.e. from one electrode, some electrodes or all of them) and sum, project or combine the resulting weighting factor vector to the velocity vector V obtained using only brain activity, the weighted velocity vector being Vw=V+w.

The new weighted velocity vector Vw is sent (arrow 210) to control the robotic exoskeleton 30. Before doing so, a security check 211 to avoid undesired velocities (exoskeleton singularities, dangerous postures for the patients, speed control, . . . ) is performed using sensor information (arrow 212) provided by the body actuators.

The patient controls his/her own upper limb movement via brain only or brain and muscle activity produced when trying to perform that exact movement. Doing so, the patient receives visual and proprioceptive feedback (arrows 220, 230, respectively) contingently and concurrently to his brain activity promoting brain plasticity.

In the following example a system hereof is used for upper limb rehabilitation.

Once a system of the present disclosure and/or subject matter is properly installed on the patient, he/she is instructed (by a screen with loudspeakers) to try to move their paretic limb as if it were healthy performing a task in several phases, producing EMG activity (if present) in the muscles affected by the paresis without producing compensatory movements. The different phases for completing the task augment in difficulty or complexity, preferably in a proximal-to-distal approach, involving at the end simultaneous coordinated multiple joint movements. That is to say, the first training stage includes movements involving more proximal muscles, such as deltoid and triceps; subsequently, proximal and distal muscles are trained, such as deltoid, triceps, biceps and hand extensors and flexors.

The tasks or exercises to be carried by the patient in this example are as follows:
1) First task, Task1: the first movement includes 2D movements in a horizontal plane. The patient uses the body actuator, for instance, an Arm-assist or Kinarm. The hybrid BMI outputs a set of kinematic features or parameters, such as the end-point velocity or joint velocities, to reach different targets in space and these are used to control each body actuator. This Task1 has six different levels:
    level 1.1: the patient starts every trial from a starting point, reaches towards the target and comes back to the initial position;
    level 1.2: the patient starts every trial from a starting point, reaches towards the target and comes back to the initial position, needing to stay within a predefined circular area around the target for a specific time, for instance, 300 ms;
    level 1.3: the patient starts every trial from a starting point, reaches towards the target and comes back to the initial position, and has to reach the target using specific velocity profiles following a rhythmic stimulation, for example, using a metronome the volume and pitch of which is gradually increased as stimulus tone, the fourth stimulus determining the time to reach the target;
    level 1.4: the targets change in the 2D space, but there is no need to come back to the initial position;
    level 1.5: the targets change in the 2D space, not needing to come back to the initial position, but having to stay within a predefined circular area around the target for a specific time, for instance, 300 ms;
    level 1.6: the targets change in the 2D space without the need to come back to the initial position, but the patient has to reach the target using specific velocity profiles following a rhythmic stimulation, for example, by a metronome the volume and pitch of which is gradually increased as stimulus tone, the fourth stimulus determining the time to reach the target.

The transition from one level to the next level within the same task occurs when an acceptable performance is reached in the previous level, for example, 75% of EMG decoding accuracy (in this case 75% has been chosen as representative of acceptable level of performance). Every session comprises 300 trials divided in 10 blocks of 30 trials.
2) Second task, Task2: after reaching the pre-established level of satisfactory performance (for instance, 75% of EMG decoding accuracy in all levels) in the previous task, Task1, the patient is asked to perform the same levels as in Task1 with an additional pronation/supination sub-task. That is to say, Task2 is the same as Task1 but additionally, when the target is reached, the patient has to do an active hand orientation movement. This hand orientation sub-task in Task2 is divided in three levels:
    level 2.1: after reaching the target in any Task1 level, the patient should perform a hand orientation movement, such as a pronation and supination movement, to satisfactorily complete the level;
    level 2.1: after reaching the target in any Task1 level, the patient should perform the supination/pronation hand movement, for example, randomly following imperative cues such as "twist your hand to the left/right" presented as pronation or supination movements respectively, and has to maintain either the hand opened or closed (randomly defined by an imperative cue) during a predefined time period, for example, 300 ms;
    level 2.3: after reaching the target in any Task1 level, the patient should orient their hand and has to reach the final supination or pronation position/angle using specific velocity profiles following a rhythmic stimulation, for example, by a metronome the volume and pitch of which is gradually increased as stimulus tone, the fourth stimulus determining the time when the complete pronation/supination position should be reached.

The hybrid BMI outputs a set of kinematic features, such as the end-point velocity or joint velocities, to reach different targets in space and orient the hand. The control of the body actuators of the upper- and fore-arm are simultaneously activated allowing for simultaneous reaching and hand orientation. Again, the transition from level to level occurs when a pre-established performance, for instance, 75%, is reached in the previous level. Every session comprises 300 trials divided in 10 blocks of 30 trials.

3) Third task, Task3: after reaching the pre-established level of satisfactory performance (for instance, 75% accuracy in all levels) in Task2, the patients is asked to perform the same levels as in Task2 with an additional grasping sub-task. That is to say, Task3 is the same as Task2 but additionally, when the target is reached and the hand has been oriented, the patient has to do an active grasping movement. This grasping sub-task in Task3 is divided in three levels:

level 3.1: after reaching the target and orienting the hand in any Task2 level, the patient should perform a grasping movement, such as an opening and closing the hand to satisfactorily complete the level;

level 3.2: after reaching the target and orienting the hand in any Task2 level, the patient should open and close their hand, and additionally, the hand should be maintained opened or closed (randomly defined by an imperative cue) during a predefined time period, for instance, 300 ms;

level 3.3: after reaching the target and orienting the hand in any Task2 level, the patient should open and close their hand, and additionally, the final open or close position has to be reached using specific velocity profiles following a rhythmic stimulation, for example, using a metronome the volume and pitch of which is gradually increased as stimulus tone, the fourth stimulus determining the time to reach the complete open/close position.

The hybrid BMI outputs a set of kinematic features, such as the end-point velocity or joint velocities, to reach different targets in space, orient the hand and control the grasping actuator. The control of the actuators of the upper- and fore-arm are simultaneously activated allowing for simultaneous reaching, hand orientation and hand opening/closing. The transition from level to level will occur when a pre-established performance, for instance, above 75% is reached in the previous level. Every session may include 300 trials divided in 10 blocks of 30 trials.

4) Fourth task, Task4: after reaching the pre-established level of satisfactory performance (above 75% of accuracy in all levels) in Task3, the patient is asked to perform: reaching, hand orientation and opening/closing of the hand, and additionally, or manipulate different objects, such as turning a door handle, eating soup, pouring water in a cup, etc.

This fourth task is especially important from a behavioural and instrumental learning point of view.

It is also important that after every rehabilitation session using a rehabilitation system hereof, at least one session takes place in which the patient tries to carry out the movements of that session, but where the hybrid BMI is partially turned off: brain and limb activities are registered, but not signals are sent to the body actuator.

In the context hereof, the term "approximately" and terms of its family (such as "approximate", etc.) should be understood as indicating values very near to those which accompany the aforementioned term. That is to say, a deviation within reasonable limits from an exact value should be accepted, because a skilled person in the art will understand that such a deviation from the values indicated is inevitable due to measurement inaccuracies, etc. The same applies to the terms "about" and "around" and "substantially".

The invention claimed is:

1. A system for motor rehabilitation of a paretic limb of a patient comprising:
   a brain machine interface;
   a first plurality of sensors couplable to pre-established positions of a head of the patient for registering brain neurosignals of the patient and to decode the brain neurosignals into movements of the body-actuator;
   a body-actuator couplable to, at least, a paretic limb of the patient;
   the first plurality of sensors being connected to the brain machine interface and the body actuator being connected to the brain machine interface;
   a second plurality of sensors which are EMG sensors couplable to the paretic limb of the patient, for registering patient EMG activity of the paretic limb of the patient; and,
   one or more devices for providing the patient with instructions relative to a series of one or both of exercises or tasks to be carried out with the paretic limb;
   upon carrying out a series of training sessions, each session comprising at least a set of such instructions, the system including, upon a registration of a significant level of decodable patient EMG activity, a switch from controlling the movements of the body-actuator based on the decoded brain neurosignals,
   to a hybrid control of the movements of the body-actuator,
      the hybrid control being an EMG-gated brain control including modulating the decoded brain neurosignals with a variable weighting factor;
      the variable weighting factor reducing the decoded brain signals during hybrid control; and,
      the variable weighting factor being a function of the decoded EMG activity of the paretic limb;
   the registration of a significant level of decodable patient EMG activity occurring when a pre-established level of decodable patient EMG activity of the paretic limb or pre-established level of decodable patient EMG accuracy between rest and activity of the paretic limb has been registered.

2. A system according to claim 1, the significant level of decodable patient EMG activity determined by comparing the decoded patient EMG activity of the paretic limb with a first reference patient EMG activity.

3. A system according to claim 2, the first reference patient EMG activity being the patient EMG activity during rest of the paretic limb or the patient EMG activity of a healthy limb.

4. A system according to claim 1, the weighting factor being a function of the difference in the decoded patient EMG activity of the paretic limb and a second reference activity model.

5. A system according to claim 4, the second reference activity model being the decoded patient EMG activity of a healthy limb of the patient, recorded prior to the training session or as retrieved from a database.

6. A system according to claim 4, the second reference activity model being the trajectory as decoded from only the brain neurosignals, and the weighting factor being a difference between this trajectory and the trajectory calculated from the decoded patient EMG activity during the same exact movement.

7. A system according to claim 1, the body actuator comprising one or both of FES or a robotic exoskeleton.

8. A system according to claim 1, each training session being divided in several phases defining completion of one or both of the exercise or task following simple to more complex movements.

9. A method for motor rehabilitation of a paretic limb of a stroke patient comprising:
disposing a hybrid brain machine interface in operative disposition relative to a patient;
coupling a body-actuator to, at least, a paretic limb of the patient;
placing a first plurality of sensors at pre-established positions of a head of the patient for registering brain neurosignals of the patient and to decode neurosignals into movements of the body-actuator;
connecting the brain machine interface to the first plurality of sensors and to the body-actuator;
placing a second plurality of sensors which are EMG sensors for registering patient EMG activity of the paretic limb of the patient and connecting this second plurality of sensors to the hybrid brain machine interface;
providing the patient with instructions relative to a series of one or both of exercises or tasks to be carried out with the paretic limb; and
carrying out a series of training sessions, each session comprising at least a set of such instructions,
when a significant level of decodable patient EMG activity has been registered,
switching from between controlling the movements of the body-actuator based on the decoded brain neurosignals, to hybrid controlling of the movements of the body-actuator, the hybrid controlling being an EMG-gated brain control including modulating the decoded brain neurosignals with a variable weighting factor; the variable weighting factor reducing the decoded brain signals during hybrid controlling; and, the variable weighting factor being a function of the decoded patient EMG activity of the paretic limb;
the registering a significant level of decodable patient EMG activity occurring when a pre-established level of decodable patient EMG activity of the paretic limb or pre-established level of between rest and activity of the paretic limb has been registered.

10. A method according to claim 9, the significant level of decodable patient EMG activity being determined by comparing the decoded patient EMG activity of the paretic limb with a first reference patient EMG activity.

11. A method according to claim 9, the weighting factor being a function of the difference in the decoded patient EMG activity of the paretic limb and a second reference activity model.

12. A method according to claim 11, the second reference activity model being the decoded patient EMG activity of a healthy limb of the patient, recorded prior to the training session or as retrieved from a database.

13. A method according to claim 11, the second reference activity model being the trajectory as decoded from only the brain neurosignals, and the weighting factor being a difference between this trajectory and the trajectory calculated from the decoded patient EMG activity during the same exact movement.

14. A method according to claim 9, further comprising removing from the patient any or all of: the first plurality of sensors, the body-actuator and the second plurality of sensors, once a plateau or a maximum level of improvement in the patient has been reached.

15. A system according to claim 1, the time elapsed between the neurosignals being registered and the neurosignals being decoded into movements of the body-actuator below 1 s.

16. A method according to claim 9, the time elapsed between the neurosignals being registered and the neurosignals being decoded into movements of the body-actuator below 1 s.

17. A system according to claim 1, the determining whether the pre-established level has been registered comprises analyzing the decoded patient EMG activity with one or more of T—student tests or with classifiers or neural networks (NNs) or with support vector machines (SVMs) to determine whether the patient EMG activity is taking place under control of the patient.

18. A method according to claim 9, the determining whether the pre-established level has been registered comprises analyzing the decoded patient EMG activity with one or more of T-student tests or with classifiers or neural networks (NNs) or with support vector machines (SVMs) to determine whether the patient EMG activity is taking place under control of the patient.

19. A system according to claim 1, the switch to a hybrid control occurring when the predefined level of decodable EMG activity in the paretic limb or the pre-established level of decodable EMG accuracy between rest and activity of the paretic limb is 65%.

* * * * *